US012584855B2

(12) United States Patent
Schade et al.

(10) Patent No.: US 12,584,855 B2
(45) Date of Patent: Mar. 24, 2026

(54) METHOD AND ARRANGEMENT FOR DETERMINING A VARIABLE OF GRAIN CROPS

(71) Applicant: DEERE & COMPANY, Moline, IL (US)

(72) Inventors: Peter Schade, Bad Dürkheim (DE); Carsten Struve, Ladenburg (DE); Renke Gralfs, Trippstadt (DE)

(73) Assignee: Deere & Company, Moline, IL (US)

( * ) Notice: Subject to any disclaimer, the term of this patent is extended or adjusted under 35 U.S.C. 154(b) by 31 days.

(21) Appl. No.: 18/488,116

(22) Filed: Oct. 17, 2023

(65) Prior Publication Data

US 2024/0159666 A1 May 16, 2024

(30) Foreign Application Priority Data

Nov. 11, 2022 (DE) .......................... 102022129876.0

(51) Int. Cl.
| | |
|---|---|
| *G01N 21/3563* | (2014.01) |
| *A01D 41/127* | (2006.01) |
| *G01N 21/359* | (2014.01) |
| *G01N 21/85* | (2006.01) |
| *G01N 33/00* | (2006.01) |

(52) U.S. Cl.
CPC ..... *G01N 21/3563* (2013.01); *A01D 41/1277* (2013.01); *G01N 21/359* (2013.01); *G01N 33/0098* (2013.01); *G01N 21/85* (2013.01); *G01N 2021/8592* (2013.01); *G01N 2201/1296* (2013.01)

(58) Field of Classification Search
CPC ........... G01N 21/3563; G01N 33/0098; G01N 2021/8592; G01N 21/85; A01D 41/1277
See application file for complete search history.

(56) References Cited

U.S. PATENT DOCUMENTS

| | | | | |
|---|---|---|---|---|
| 5,343,761 A | * | 9/1994 | Myers ..................... | G01F 1/206 |
| | | | | 73/861.73 |
| 2005/0085283 A1 | * | 4/2005 | Kormann ............. | A01D 43/085 |
| | | | | 460/7 |
| 2017/0045444 A1 | * | 2/2017 | Haiges ................. | G01N 21/359 |
| 2018/0164471 A1 | * | 6/2018 | Dybro ................... | G01B 21/22 |

(Continued)

FOREIGN PATENT DOCUMENTS

| | | |
|---|---|---|
| CA | 2182989 C | 3/2001 |
| CN | 110132384 A | 8/2019 |
| CN | 112304947 A | 2/2021 |

(Continued)

OTHER PUBLICATIONS

EP4029364A1 English Translation (Year: 2022).*

(Continued)

*Primary Examiner* — Hina F Ayub
*Assistant Examiner* — Kaitlyn E Kidwell
(74) *Attorney, Agent, or Firm* — HANLEY, FLIGHT & ZIMMERMAN, LLC

(57) ABSTRACT

A method for measuring at least one of a mass-specific or size-specific variable of grain crops, the method comprising the following steps: recording a spectrum of the grain crops with a sensor operating in the near-infrared range; and deriving the at least one of mass-specific or size-specific variable from the spectrum.

20 Claims, 4 Drawing Sheets

(56) References Cited

U.S. PATENT DOCUMENTS

| | | | | |
|---|---|---|---|---|
| 2021/0247305 A1* | 8/2021 | Schade | .................... | G06N 3/08 |
| 2022/0053692 A1* | 2/2022 | Fischer | ................. | G06V 20/68 |

FOREIGN PATENT DOCUMENTS

| | | | | | |
|---|---|---|---|---|---|
| DE | 0157483 | A | 11/1982 | | |
| DE | 3420800 | A1 | 1/1985 | | |
| DE | 0277756 | A1 | 4/1990 | | |
| DE | 29709234 | U1 | 11/1997 | | |
| DE | 19645068 | C1 | 4/1998 | | |
| DE | 19922867 | A1 | 11/2000 | | |
| DE | 102004048103 | A1 | 4/2006 | | |
| DE | 102022110185 | A1 | 11/2023 | | |
| EP | 1305994 | A1 | 5/2003 | | |
| EP | 1516522 | A2 | 3/2005 | | |
| EP | 2189781 | A2 | 5/2010 | | |
| EP | 2742791 | A2 | 6/2014 | | |
| EP | 3008990 | A2 | 4/2016 | | |
| EP | 3366104 | A1 | 8/2018 | | |
| EP | 3901588 | A1 | 10/2021 | | |
| EP | 4029364 | A1 * | 7/2022 | ......... | A01D 41/1272 |
| JP | 2023125301 | A | 9/2023 | | |
| KR | 20160037507 | A | 4/2016 | | |
| WO | WO 8605353 | A1 | 9/1986 | | |
| WO | WO 2018073093 | A1 | 4/2018 | | |
| WO | WO 2018073163 | A1 | 4/2018 | | |
| WO | WO 2019014997 | A1 | 1/2019 | | |

OTHER PUBLICATIONS

Extended European Search Report and Written Opinion issued in European Patent Application No. 23206363.6 dated Apr. 15, 2024, in 15 pages.

W. Wu et al., GainTKW: A Measurement System of Thousand Kernel Weight Based on the Android Platform, Agronomy 2018, 8, 178, Sep. 10, 2018, pp. 1-15.

Hilliard, J. et al., Starch content, test weight, and other quality parameters of corn produced in different maturity areas of Ontario, Crop Science vol. 14,4 (1974), Jul. 1, 1974, pp. 546-548.

Dobre, P.S. et al., Protein content, thousand kernel weight (tkw) and volumetric mass (vm) variability in a set of wheat mutated and mutated/recombinant dh lines, AgroLife Scientific Journal, vol. 5, Nr. 1, 2016, pp. 59-62.

* cited by examiner

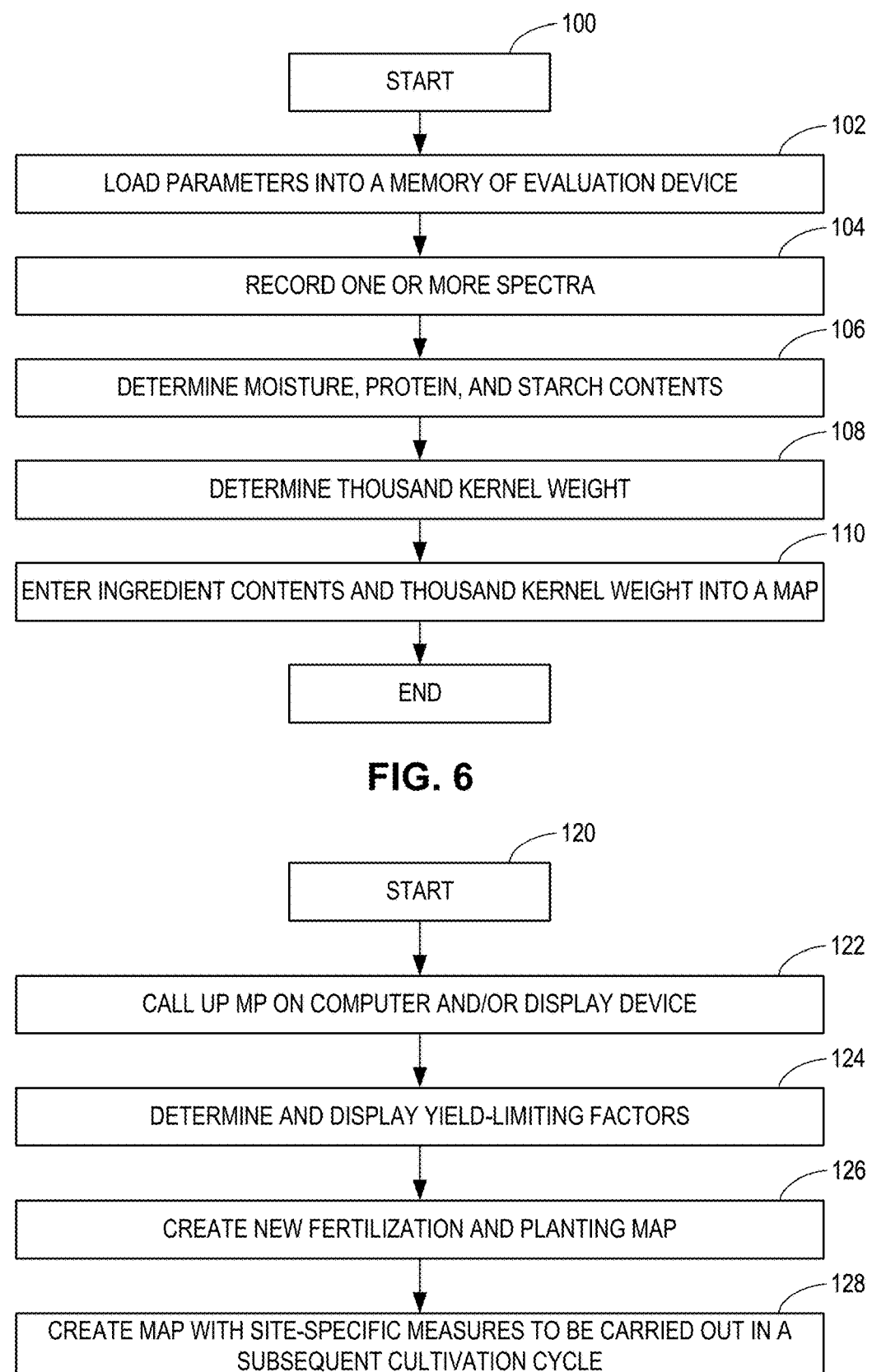

100

START

102

LOAD PARAMETERS INTO A MEMORY OF EVALUATION DEVICE

104

RECORD ONE OR MORE SPECTRA

106

DETERMINE MOISTURE, PROTEIN, AND STARCH CONTENTS

108

DETERMINE THOUSAND KERNEL WEIGHT

110

ENTER INGREDIENT CONTENTS AND THOUSAND KERNEL WEIGHT INTO A MAP

END

START

122

CALL UP MP ON COMPUTER AND/OR DISPLAY DEVICE

124

DETERMINE AND DISPLAY YIELD-LIMITING FACTORS

126

CREATE NEW FERTILIZATION AND PLANTING MAP

128

CREATE MAP WITH SITE-SPECIFIC MEASURES TO BE CARRIED OUT IN A SUBSEQUENT CULTIVATION CYCLE

FIG. 7

METHOD AND ARRANGEMENT FOR DETERMINING A VARIABLE OF GRAIN CROPS

RELATED APPLICATIONS

This document claims priority based on German Patent Application No. 102022129876.0, filed on Nov. 11, 2022, which is hereby incorporated by reference into this application.

DESCRIPTION

The present disclosure relates to a method and an arrangement for determining a mass-specific and/or size-specific variable of grain crops.

BACKGROUND

Modern precision farming strives to make optimum use of the available resources, such as water, soil, seed and fertilizer, in order to exploit the yield potential to the greatest possible extent, with minimum consumption of resources. In some approaches, yield maps are generated during harvesting by means of suitable measuring equipment with simultaneous determination of position, in order to vary, for example, fertilizer quantities and seed rates on the basis of the yields in a site-specific manner (e.g., WIPO Patent Appl. No. WO 86/05353 A1). Refinement of the planning of subsequent precision farming measures is made possible by measuring ingredients, such as starch and protein contents, of the crop (e.g., European Patent Appl. No. EP 2 189 781 A2). However, these approaches are generally not suitable for determining in a relatively simple manner one or more of said mass-specific variables (thousand kernel mass, density, dimensions of the grains) or any other information from which one or more of said quantities could be derived.

BRIEF DESCRIPTION

A method for measuring at least one of a mass-specific or size-specific variable of grain crops, comprising the following steps: recording a spectrum of the grain crops with a sensor operating in the near-infrared range; and deriving the at least one of mass-specific or size-specific variable from the spectrum.

An apparatus for measuring at least one of mass-specific or size-specific variable of grain crops in a field, comprising: a sensor operating in the near-infrared range configured to record a spectrum of the grain crops; and an evaluation device configured to derive the at least one of mass-specific or size-specific variable from the spectrum.

DRAWINGS

The above-mentioned aspects of the present disclosure and the manner of obtaining them will become more apparent and the disclosure itself will be better understood by reference to the following description of the examples of the disclosure, taken in conjunction with the accompanying drawing, wherein:

FIG. 6 shows a flow chart regarding the procedure for measuring the thousand kernel weight; and FIG. 7 shows a flow chart for evaluating the measured thousand kernel weight.

DETAILED DESCRIPTION

Figure 1:
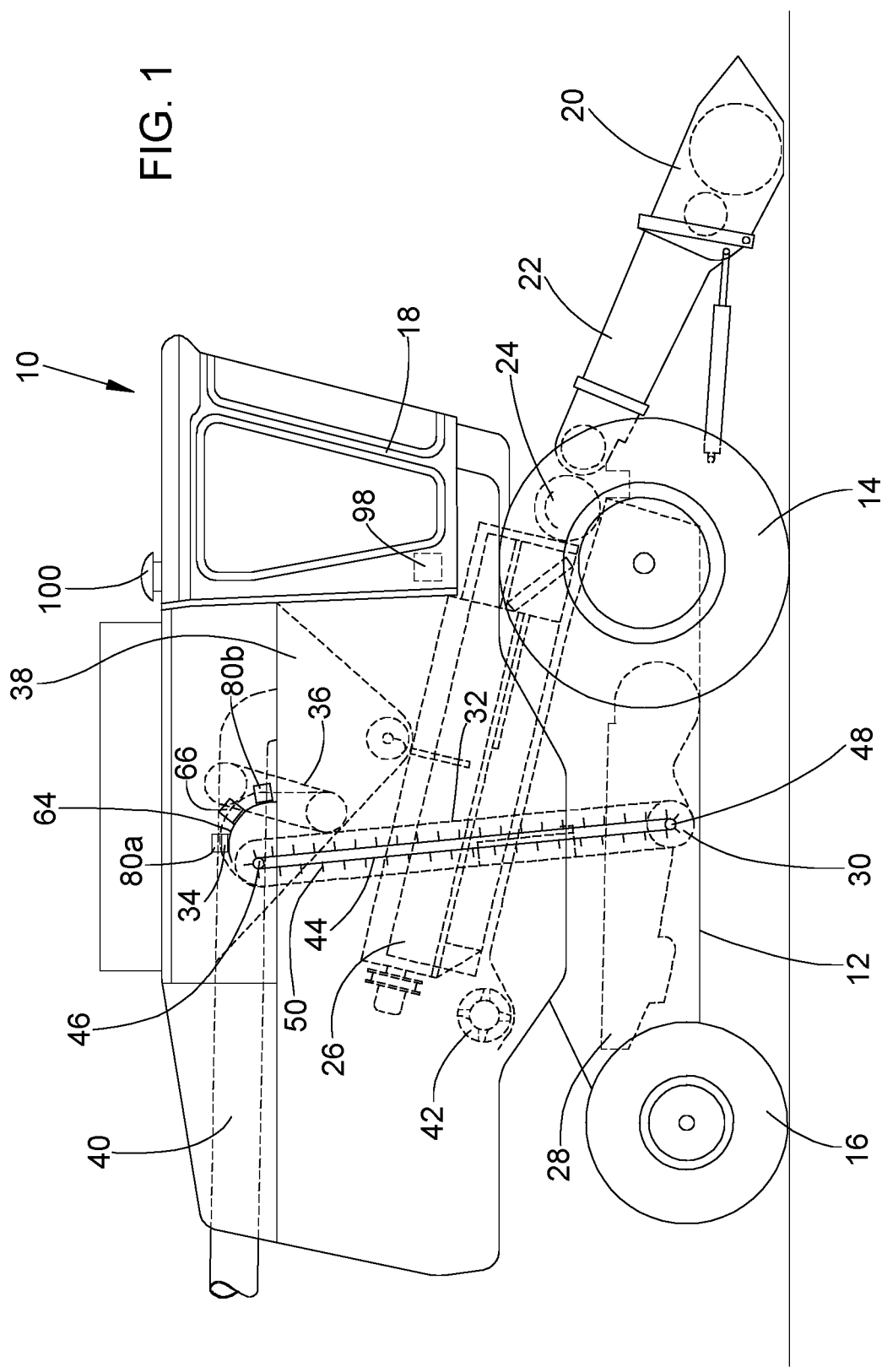
FIG. 1 shows a schematic side view of a harvester with a measuring arrangement for spectroscopic examination of a crop stream.

The present disclosure provides a method and an arrangement for measuring a mass or size-specific variable of the grain crops during grain harvesting, said method and arrangement allowing for more detailed information about the crop. The method and arrangement should also make it possible to determine the appropriate planting (i.e., sowing or seeding) rate or correct fertilizer rates for spring fertilization.

In one example, the mass-specific variable (thousand kernel weight, density, hectoliter weight) and/or size-specific variable (dimensions) is determined on the basis of spectra of the grain crops, which will be referred to as grains or grain in the following. Further, the content of ingredients of the grain crops can be determined on the basis of the spectrum and the mass-specific and/or size-specific variable can be determined on the basis of the determined content. These ingredients are, in particular, water, protein and starch or are correlated therewith, as is the case, for example, with gluten correlated with protein.

In another example, the mass-specific and/or size-specific variable can be calculated directly on the basis of the spectrum using calibration data, i.e., without determining the ingredients. The mass-specific and/or size-specific variable can be determined continuously during harvesting of the grain crops by means of a harvester on a different crop in each case and can be recorded georeferenced in a map. However, a mobile or stationary application of the method and the associated device at any location is also possible. In addition, at least one ingredient of the crop can be measured and stored georeferenced in the map together with the mass-specific and/or size-specific variable. In addition, the yield can be measured subarea-specifically and can be stored georeferenced in the map together with the mass-specific and/or size-specific variable. The map can be used for planning agronomic measures.

Although previous approaches measure yields and, where applicable, the ingredients of the crop on a site-specific basis, an essential aspect remains unconsidered when harvesting grain crops, such as cereal or corn, namely the size, dimensions or mass of the individual grains (which is usually measured as the so-called thousand kernel mass (or thousand kernel weight)), or the number of grains per unit area of the field. The yield, i.e., the mass of the grains (hereinafter multiple grains are also referred to as "the grain") per unit area of the field, which is already measured in previous approaches on a site-specific basis, can be calculated by multiplying the number of grains per unit area by the thousand kernel mass (divided by 1000). The thousand kernel mass is usually measured by counting 1000 grains and measuring their mass (alternatively, the volume of 1000 grains could be multiplied by their mass density (mass per volume)). If any two of the agronomic variables of yield, mass (or thousand kernel mass or volume and density of individual grains) of the individual grains, and number of grains per area are known, the third agronomic variable can be calculated. So far, however, only one measurement of yield is provided.

The grain size or thousand kernel mass or dimensions of the grains contain important information for the farmer because, for example, a high thousand kernel mass or relatively large grains with low yields may or may not indicate that yields could be increased by increasing the number of grains per area because more resources are available at the site in question than have been used by the harvested plants, while relatively small thousand kernel masses or relatively small grains indicate excessively high grain numbers per area, since fewer resources are available at the site in question than would be needed to allow all grains potentially coming to maturity to actually mature. The components of grain number per area and thousand kernel mass can be influenced by adjusting the planting rate (seeds/plants per area) and the spring fertilization (influencing the tillering and thus the number of ears/cobs/pods per area and number of grains per ear/cob/pod). Planting rates can be used to influence the number of seeds planted per area, since more grains sown result in more stalks per area, which in turn results in more ears/cobs/pods and thus more grains per area. This process is equally true in reverse.

Also, the tillering of the plant (denotes the stage of branching growth) can be influenced. The number of ears formed in the case of cereals can be influenced by spring fertilization. If this fertilization is increased, the plant will form more shoots; conversely, if fertilization is reduced, fewer shoots will be formed. These shoots then form ears in the later course of growth, but also form leaf mass that evaporates water and can thus cause premature maturity if the leaf mass is too high.

Spring fertilization also determines the number of grains per ear, cob or pod. By means of this mechanism, therefore, the grain number per area can also be influenced, since with more shoots more ears and thus more grains are formed. The number of grains per area also changes the thousand kernel mass (the more grains, the lower the thousand kernel mass, and vice versa if water is a limiting factor). For each site, there is an optimal relationship between the grain number per area and the thousand kernel mass. Yield is made up of these two components. So far, however, only the yield is measured, without knowing how the components of grain number and thousand kernel mass behave and which factor may have been limiting the yield. Thus, no statement can be made about the correct planting rate or a suitable dosage of fertilizer because individual components of the yield cannot be determined in the area.

Up to now, the thousand kernel mass—for the purpose of displaying the loss or tailings of the grain volume—was assumed to be constant in the case of a combine harvester (e.g., European Patent Appl. No. EP 1 516 522 A2, German Patent Appl. No. DE 34 20 800 A1) and, if necessary, was counted prior to harvesting. In addition, acquisition of grain dimensions using a camera and image processing for yield prediction on crops growing in a field (e.g., WIPO Patent Appl. No. WO 2018/073163 A1, WIPO Patent Appl. No. WO 2018/073093 A1) or for loss grains (e.g., European Patent Appl. No. EP 2 742 791 A2) and optical acquisition of harvested grains and evaluation to determine thousand kernel mass under laboratory conditions (e.g., German Patent Appl. No. DD 277 756 A1, German Patent Appl. No. DD 157 483 A1, German Patent Appl. No. DE 297 09 234 U1, German Patent Appl. No. DE 196 45 068 C1, Chinese Patent Appl. No. CN 110132384 A and W. Wu et al., GainTKW: A Measurement System of Thousand Kernel Weight Based on the Android Platform, Agronomy 2018, 8, 178) have been described.

Previous measurements of starch and protein contents and thousand kernel weights of certain wheat cultivars have not shown any significant correlation between these variables (e.g., Dobre, P. S. et al, Protein content, thousand kernel weight (tkw) and volumetric mass (vm) variability in a set of wheat mutated and mutated/recombinant dh lines, AgroLife Scientific Journal, Volume 5, No. 1, 2016, pages 59-62), with the situation being similar also for the correlation between protein and starch content on the one hand and density and thousand kernel weight on the other hand in the case or corn (e.g., Hilliard, J. et al., Starch content, test weight, and other quality parameters of corn produced in different maturity areas of Ontario, Crop Science Vol. 14.4 (1974), pages 546 to 548).

In another example, the present disclosure relates to the determination of the thousand kernel weight (and/or mass density, for example hectoliter weight) and/or the dimension of grains by means of a spectroscopic measurement. In the exemplary example, this measurement is performed on a harvester, which allows mapping of the measured values. However, it would also be possible to carry out a measurement with a mobile or stationary spectrometer, for example in a laboratory, in or on a transport vehicle or a storage facility for grain.

Agricultural Machine

FIG. 1 shows a self-propelled agricultural harvester 10 in the form of a combine harvester, having a frame 12 on either side of which there are mounted front wheels 14 in engagement with the ground for propelling the harvester 10 in a forward direction, which in FIG. 1 is to the right, and also rear steerable wheels 16. Operation of the harvester 10 is controlled from the operator's cab 18. In harvesting operation, a cutting unit 20 is used to harvest grain-containing crop and to feed it to an inclined conveyor 22. The harvested product is fed by the inclined conveyor 22 to a guide drum 24, which feeds the crop to an axial crop-processing device 26. In the following, directional indications, such as front and rear, refer to the forward direction of the harvester 10.

The crop processing unit 26 comprises a rotor housing and a rotor arranged therein, to which crop-processing elements are attached. Instead of an axial crop-processing unit 26, a tangential threshing drum and an axial separator or straw walker following it can also be used. Grain and chaff that fall through a threshing concave and a separating grid are fed to a cleaning system 28 with a blower and lamella sieves that can be set in an oscillating motion. The cleaning system 28 removes the chaff and feeds the clean grain via an auger conveyor 30 to a clean grain elevator 32, which conveys the clean grain to a transfer housing 34, from which it is conveyed by another auger conveyor 36 to a grain tank 38. The clean grain in the grain tank 38 can be unloaded onto a grain truck, trailer or lorry by an unloading auger conveyor 40. Threshed straw leaving the crop-processing device 26 is ejected from the crop-processing device 26 through an outlet and is fed to an ejector drum 42, which ejects the straw to the rear or feeds it to a straw chopper (not shown).

Figure 2:
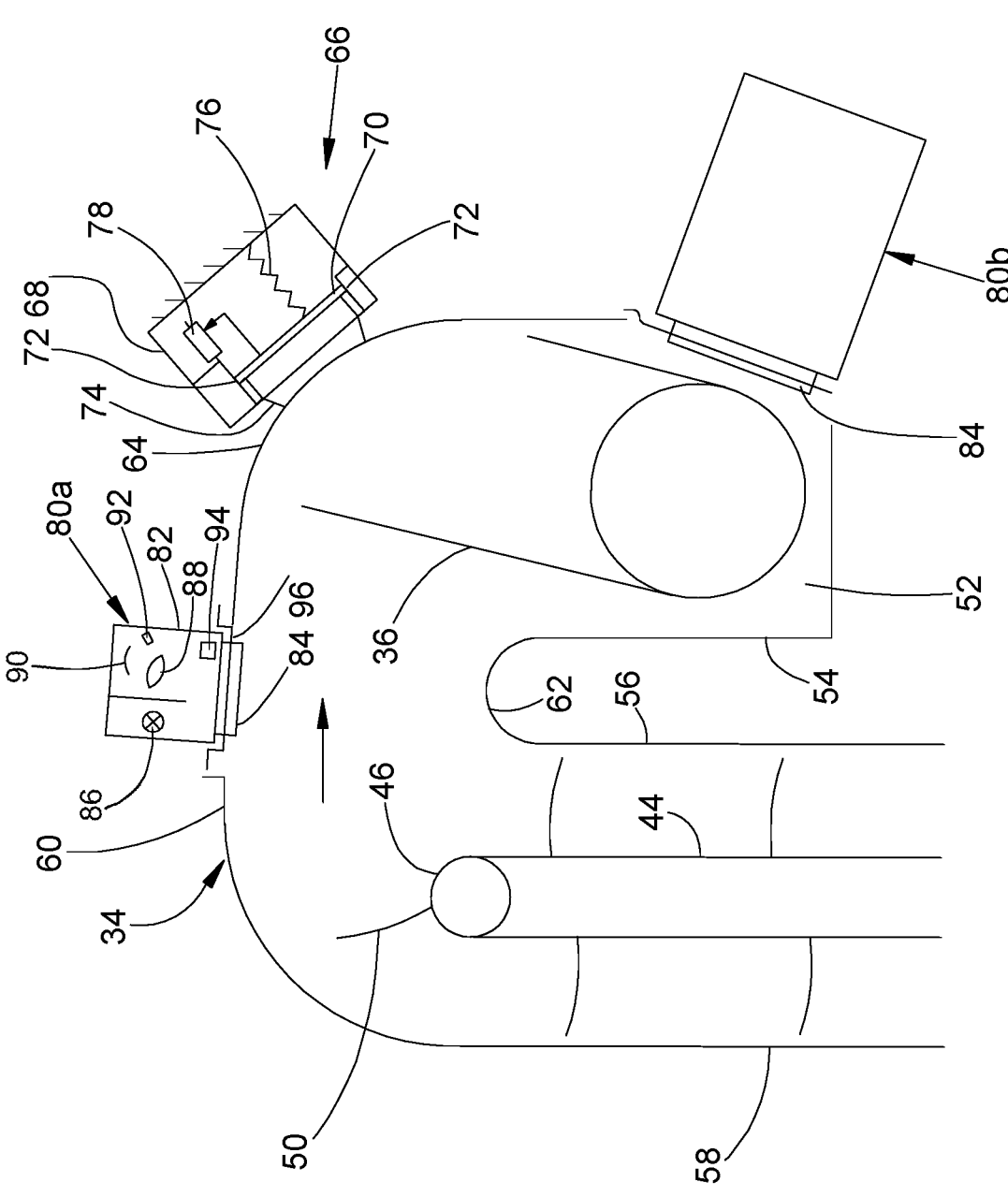
FIG. 2 shows an enlarged side view of the outlet region of the grain elevator of the harvester of FIG. 1.

FIG. 2 shows the transfer housing 34 in an enlarged view. The elevator 32 is in the form of a paddle conveyor and comprises one or more chains 44, which rotate around an upper return wheel 46 and a lower return wheel 48, one of which is driven. The chain 44 carries a plurality of scoop-like paddles 50, which discharge the upwardly conveyed grain above the upper return wheel 46 approximately horizontally. The transfer housing 34 comprises a trough 52, in which the inlet of the further auger conveyor 36 is located, and which is bounded by a wall 54 downwardly and toward the elevator 32. The lateral part of the wall 54 is connected by a roof-shaped portion 62 to a rear wall 56 of a housing of the elevator 32, which is enclosed to the front by a front wall 58. The front wall 58 transitions in a curved fashion at its upper side into a cover 60 of the transfer housing 34. On the side opposite the outlet of the elevator 32, the transfer housing 34 is bounded upwardly and to the front by a concavely curved baffle plate 64 of a throughput determination device 66, against which the grain discharged from the elevator 32 impinges.

The throughput determination device 66 further comprises a housing 68, which is positioned on the outside of the baffle plate 64 and of the transfer housing 34 and which is rigidly connected to the frame 12. A plate 70 is slidably mounted in the housing 68 by guides 72 in a direction running obliquely upwards and forwards. The plate 70 is rigidly connected to the baffle plate 64 by a tube 74 and can move with the baffle plate 64 and the tube 74 relative to the housing 68. A spring 76 biases the plate 70 downwardly and to the rear, so that the plate 70 is moved upwardly and to the front against the force of the spring 76 by grain impinging on the baffle plate 64. A position sensor 78 in the form of a potentiometer senses the position of the plate 70 and, consequently, the baffle plate 64, so that its output signal is a measure of the mass flow rate of the crop stream discharged from the elevator 32.

Sensing Device

Furthermore, a sensing device—shown as spectrometers 80a, 80b—are shown at two different positions in FIGS. 1 and 2. Usually, only one of the spectrometers 80a or 80b is installed. The two shown spectrometers 80a, 80b serve to illustrate different positioning possibilities. The spectrometers 80a, 80b are of identical construction, which will be discussed below with reference to the spectrometer 80a. The spectrometer 80a comprises a housing 82 having an opening in which there is arranged a window 84, the pane of which is preferably made of sapphire glass or another material that is sufficiently resistant to wear and sufficiently transparent in the wavelength range of the light used for the examination. Inside the housing 82 there is a light source 86, which, through the window 84, irradiates the crop stream discharged from the elevator 32 with broadband light, so-called white light, generally covering the near-infrared range. Light reflected from the crop stream re-enters the housing 82 through the window 84, where it is directed by a lens system 88 onto a dispersive element 90 in the form of a concave mirror with a grating structure attached to its underside, which deflects the light in directions dependent on the wavelength, and finally reaches a detector 92 having a series of light-sensitive elements which emit signals dependent on the intensity of the received light. The method described herein is just one possible example of a spectrometer arrangement for measuring ingredients in agricultural products. It is also possible for the light source to be arranged opposite the window 84, so that light passing through the crop impinges on the lens system. It is also possible to measure in a spherical arrangement (e.g., WIPO Patent Appl. No. WO 2019/14997 A1). The dispersive element can also be embodied in a different way, for example as a transmission grating or it can be a MEMS. An evaluation device 94 connected to the detector 92 evaluates the output signals of the detector 92 and provides spectra and/or information derived therefrom, for example fractions of ingredients in the crop stream. Suitable spectrometers are described in German Patent Appl. Nos. DE 199 22 867 A1 and DE 10 2004 048 103 A1, the disclosures of which are included by reference in the present documents.

The spectrometer 80a is disposed above the cover 60 of the transfer housing 34, with the window 84 being located within an opening in a ramp 96 which is disposed immediately upstream of the baffle plate 64. The ramp 96 serves to direct the crop stream discharged from the elevator 32 towards the baffle plate 64 and, in particular, to prevent grain at the leading edge of the baffle plate 64 with respect to the crop stream from reaching the outer side of the baffle plate, which would be undesirable. Thanks to an adjustment of the ramp 96 and the window 84 by a relatively small angle, which can be, for example, between 3 and 5°, a self-cleaning function of the glazing or pane of the window 84 of the spectrometer 80a is achieved by the mass flow of the crop. A soiling or accumulation of deposits of crop residues or other dirt particles on the pane of the window 84 is thus counteracted.

The spectrometer 80b, on the other hand, is located at the downstream end of baffle plate 64, with the window 84 extending obliquely downward and to the rear towards the center of the trough 52. The crop stream flows past the windows 84 of both spectrometers 80a, 80b so that any impurities are carried along and do not adhere to the windows 84.

The evaluation device 94 of the spectrometer 80a or 80b and the position sensor 78 of the throughput determination device 66 are connected via a bus system or an associated cable or via radio or optically to a recording device 98, which is located in the operator's cab 18; cf. FIG. 1. The recording device 98 is furthermore connected to a position determination device 100 in the form of an antenna and receiving devices for receiving and processing signals of a satellite-based position determination system, for example GPS and/or Glonass and/or Eureka. Accordingly, the signals of the evaluation device 94 of the spectrometer 80a or 80b and of the position sensor 78 of the throughput determination device 66 are recorded in a georeferenced manner by the recording device 98 for later use for accounting purposes or for use in precision farming. In addition, these signals can be used to automatically adjust components of the harvester 10, for example to adjust the fan speed and sieve opening width of the cleaning system 28 or the speed of the axial crop-processing device 26. Placing the spectrometer (or spectrometers) 80a and/or 80b and the throughput determination device 66 in close proximity to each other has the advantage that measured values of the same crop are recorded in each case, i.e., that the temporal correlation of the measured values is very good. However, it would also be possible to mount the spectrometer 80a or 80b at any other location on the harvester 10, for example on the elevator 32 or a separate measuring chamber which can be filled by the elevator 32 (e.g., Canadian Patent Appl. No. CA 2 182 989 C or European Patent Appl. No. EP 1 305 994 A1) or on the auger conveyor 30.

Evaluation of the Spectra

The objective of the present disclosure is to determine a mass-specific and/or size-specific variable of the harvested grain, for example its thousand kernel weight, mass density and/or dimensions. The size (dimensions, i.e., length and/or diameter and/or volume) of the grains and the mass measured in kg or g or the weight of the individual grains measured in N (Newton) varies not only depending on the type of crop, but also depending on the particular location, because the grains become larger or smaller according to the site, depending on the supply of water, light, soil properties, crop density, fertilization, etc. In addition, depending on local conditions, more or fewer plants grow, with more or fewer grains growing on them. As a result, the yield also varies, which can be calculated as the product of the number of grains per unit area with their respective mass. For agronomic purposes, it is therefore beneficial to obtain a map in terms of a variable dependent on the mass and/or size of the grains, on the basis of which subsequent actions can be planned site-specifically. Said size is in particular the thousand kernel mass, which is an agronomically common size.

In previous approaches, a measurement of ingredients (protein and starch content) in grain is already known and established. For this purpose, near-infrared spectroscopy is usually used. Here, the relative moisture, starch or protein fraction (in percent) in the dry or total mass of a sample is measured. For this purpose, calibration data are stored in the evaluation device 94 of the spectrometer 80*a* and/or 80*b*, on the basis of which the measured spectra are converted into said ingredient fractions. This evaluation (also with respect to the other agronomic data discussed below) can also be carried out in the recording device 98 or any other computer on the harvester 10 or a computer spaced therefrom, to which the spectra are transmitted wirelessly, or the spectra are first recorded (in particular georeferenced) and later evaluated on any computer.

Since the grain weight is a structural parameter and not a chemical variable, it cannot prima facie be assumed that thousand kernel weight or any related agronomic variable (especially the mass density or hectoliter weight of the grain or its dimensions) could be measured by a near-infrared spectrometer (e.g., the measurements of Dobre et al. and Hilliard et al., Op. cit.).

Closer examination, however, shows surprisingly that, due to the physiology of plant growth, it is nevertheless possible to estimate the grain weight on the basis of ingredient values and thus the grain weight can be recorded at least approximately on the basis of ingredient sensors. The reason for this is that wheat grains, for example, form internal protein cores of similar size. The starch body grows around the protein grains and its final size depends on the nutritional status of the individual plant. For this reason, a heavy and large grain typically has a high starch to protein ratio and a lightweight and small grain has a low starch to protein ratio.

Figures 3, 4, 5:
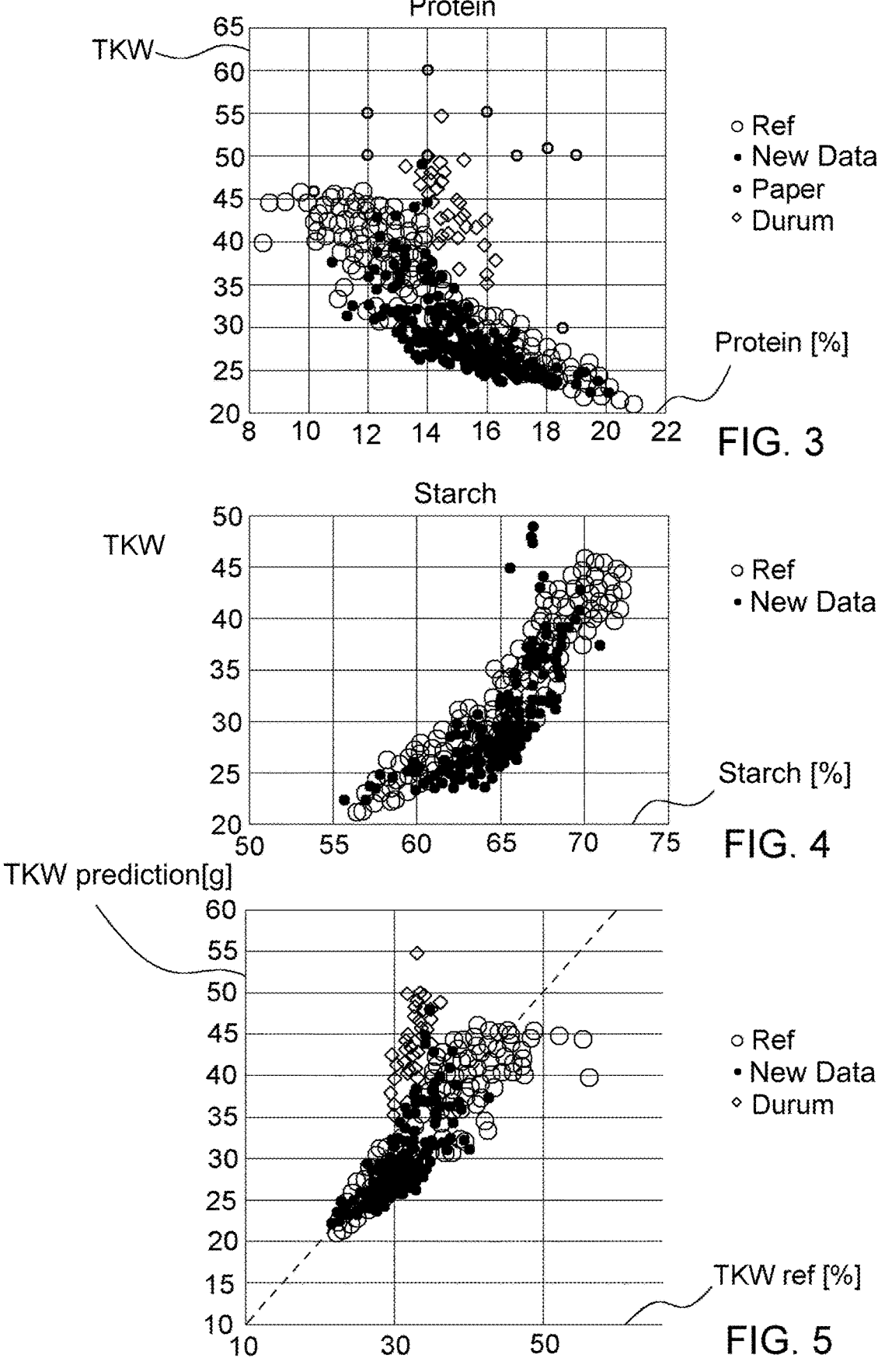
FIG. 3 shows a graph illustrating the relationship between thousand kernel weight (TKW) and protein content for a number of measured values.
FIG. 4 shows a graph illustrating the relationship between thousand kernel weight (TKW) and starch content for a number of measured values.
FIG. 5 shows a graph illustrating the relationship between measured and spectra-based thousand kernel weights (TKW)

For this purpose, reference is made to FIGS. 3 and 4, in which measured values for protein content and starch content, respectively, and thousand kernel weight (TKW) are plotted for different samples. The different points represent a reference measurement (i.e., a number of measured values from a specific wheat cultivar used to create calibration data), new data for the same cultivar (determined later), as well as data from Durum wheat and some measured values from Dobre et al. It can be seen that certain correlations are evident in measurements within a cultivar or even within grains of similar variety. For example, thousand kernel weight decreases with increasing protein content, while it increases with increasing starch content. In the measurements for Durum and those of Dobre et al. other coefficients would appear to be useful in the evaluation.

Mathematical approaches were used to create a suitable equation based on the reference measurement, which can be used to model the thousand kernel weight (TKW):

$$TKW \sim c0 + c1 * \text{starch}[\%]/\text{protein}[\%] + c2 * \text{moisture}[\%]/(\text{protein}[\%] * (1 - \text{moisture}[\%]/100)) \quad (1)$$

A corresponding curve is shown in FIG. 5, comparing measured thousand kernel weights and those measured using equation (1). The coefficients c0, c1 and c2 used for this purpose were determined with the reference material and applied to samples of the same grain cultivar (new data). A useful correlation is obtained for the reference measurement and the new data. Accordingly, it is possible to determine the thousand kernel weight on the basis of the spectra measured with spectrometer 80*a* or 80*b*. Durum is a different cultivar, as is also the grain studied in the paper by Dobre et al. The plot shows that the coefficients c0, c1 and c2 are unsuitable for Durum and corresponding adjusted coefficients still have to be determined.

Accordingly, the protein and starch content are determined by the ingredient sensor (spectrometer 80*a*, 80*b*) with respect to the dry mass and the moisture content is determined with respect to the total mass. The constants c0, c1 and c2 can be determined by calibration measurements for a particular cultivar of grain to be studied. They are different for different cultivars, and it may also be the case that other equations have to be used for other cultivars or types of grain.

The relation between thousand kernel weight and ingredients, instead of using equation (1), can also be modeled or learned by more general functions, such as neural networks, or the thousand kernel weight could be determined directly from the NIR spectra (similarly to the previous approach of determining ingredients on the basis of spectra by calibration data generation).

A possible approach for measuring and mapping the thousand kernel weight is shown in FIG. 6. After the start in step 101, in step 102 the parameters for the particular harvested crop (grain cultivar) are loaded into a memory of the evaluation device 94. The parameters include calibration data for converting the spectra into moisture, protein and starch contents and the constants c0, c1 and c2 of equation (1). In step 104, one or more spectra are recorded; in step 106, the moisture, protein, and starch contents are determined on the basis of the spectrum or spectra and the calibration data; and in step 108, the thousand kernel weight (TKW) is determined using equation (1). In step 110, the ingredient contents and the thousand kernel weight are entered into a map in a site-specific manner, using position signals from the position determination device 100. Step 110 is again followed by step 104, unless the process is completed when the field is harvested. The determination and mapping of thousand kernel mass can also be done downstream, for example in a farm management information system. For this purpose, protein, starch and moisture (or the spectra) can be mapped and evaluated later.

In step 108, a referencing of the determined thousand kernel weight to the site where the grains have grown can be carried out in a manner (e.g., European Patent Appl. No. EP 3 008 990 A2), i.e., the running time of the crop between harvesting and sensing and the distance covered in the meantime by the harvester 10 or position determination device 100 can be compensated.

In addition, the yield (in volume or mass per unit area) can be measured and mapped by means of the throughput determination device 66 (e.g., European Patent Appl. No. 3 901 588 A1) and other references cited therein) and the mass density (hectoliter weight or the like) of the grain can be calculated on the basis of the yield and the thousand kernel weight. Alternatively, or additionally, the number of grains per unit area of the field can be determined on the basis of the yield and the thousand kernel weight. In this regard, reference is made to the earlier patent application German Patent Appl. No. DE 10 2022 110 185.1, the disclosure of which is included by reference in the present documents.

The thousand kernel weight is also correlated with the density (hectoliter weight), so that the latter could also be determined by an adapted model on the basis of the spectra or ingredients. Analogously, the spectra also contain information about the dimensions of the grains due to the correlations between ingredients and dimensions discussed above. These can therefore be determined, analogously to the approach for the thousand kernel weight, on the basis of the spectra, either via the detour with the ingredients or directly on the basis of the spectra through corresponding calibration data.

Additional Uses of TKW

The map obtained according to the approach of FIG. 6 can be sent by remote data transmission or by a portable storage to a stationary or mobile computer of a farmer or agronomist and used for planning agronomic measures. Here, the measure may be planned based on the mass of the grains and/or the number of grains per unit area and/or their dimensions (each of which may be calculated on the basis of the other variables and the yield or, in the case of the dimensions, determined directly on the basis of the spectra as described in the preceding paragraph). In particular, the planting rate can be planned based on the number of seeds per unit area and/or their dimensions and/or their mass.

FIG. 7 shows a possible approach for using the map generated by the approach according to FIG. 6. After starting in step 120, in step 122 the map is called up on any computer, i.e., loaded into its memory. The computer may be a stationary computer located in the office of the farmer or appointed agronomist whose field has been harvested by the harvester 10 according to the approach of FIG. 6, or the farmer or appointed agronomist may use a mobile computer (laptop, tablet, smartphone, etc.). The map may also be displayed two-dimensionally on a display device in step 122, with different thousand kernel masses (or any other variable representative of the dimensions or mass or weight of the grains or their number per area) indicated by colors or otherwise (grayscale, shading, etc.). Also, the map may include one or more ingredient contents of the crop that were measured by the near-infrared sensor 80a, 80b and mapped in a site-specific manner. This one or more ingredient content, for example protein content of the crop, may also be displayed. Analogously, one or more other characteristics of the field, for example soil type or fertilizer applications that vary site-specifically or are constant across the field, or measured nutrients in the soil, or the yield (in grains or mass per unit area), or the number of plants sown per unit area in each case, may also be displayed.

In step 124, yield-limiting factors can be determined and displayed using said map and, in particular, the thousand kernel masses recorded site-specifically or any other variable or variables representative of the dimensions or mass or weight of the grains or their number per unit area. In addition, the yield per unit area (also measured and recorded site-specifically in the approach according to FIG. 6 with the throughput determination device 66) can be displayed and/or used to calculate the number of grains per unit area on the basis of the thousand kernel masses.

By documenting the (thousand) kernel mass and/or the grain volume, it is possible to define at which point of the field the yield was composed and in what way. Thus, a given yield may be based on a larger number of smaller grains per area or a smaller number of larger grains per area. To further explain this, for example, a calculation of the number of grains per area can be performed by dividing the yield, also mapped site-specifically and measured in units of mass per area, which can be measured, for example, by the throughput determination device 66 in the grain elevator 32, by the mapped (thousand) grain mass.

The calculated number of grains per area and/or their dimensions or mass can be used to draw conclusions as to whether possible potential was wasted during plant cultivation. Thus, few, large grains indicate that there is still potential for a higher yield. In this case, the planting rate could be increased, or the plant's tillering could be influenced by sufficient spring fertilization, i.e., more plants per unit area could be grown at the site in question in the future. On the other hand, many, small grains (shriveled grains) indicate that there are too little water/nutrients to feed the number of plants grown per unit area. In this case, the planting rate would have to be reduced and/or fertilization and, if necessary, water supply adjusted. To easily identify such issues, a map can be displayed showing the thousand kernel mass divided by the number of grains per unit area (or the reciprocal thereof). High values for thousand kernel mass divided by the number of grains per unit area would prompt an increase in the planting rate/strengthening of the tillering, and small values would prompt a decrease. The described recording and mapping of thousand kernel mass and/or dimensions of grains and/or numbers of grains per unit area thus helps the farmer or agronomist to adapt crop management measures to changing soils and conditions.

In step 124, a map with the limiting factors can be created. This map can show, on a site-specific basis, where which agronomic measure was lacking or can be improved. Specifically, missing or excess fertilizer can be identified based on protein content, missing or excess water can be identified based on grain size, and excessive or low planting rate/shoot formation (tillering) can be identified based on thousand kernel mass and number of grains per area.

Accordingly, a new fertilization and planting map is created in step 126, into which the conclusions from step 124 are incorporated. Here, the farmer or appointed agronomist can use the displayed data to determine which measures are appropriate where, either qualitatively or quantitatively. However, a computer-aided algorithm can also be used here, which in particular works in a self-learning manner, i.e., learns gradually, on the basis of previous measures and their measured effect, which measures are sensible in the field concerned.

The map created in the described manner with the site-specific measures to be carried out is taken into account in step 128 in a subsequent measure, in particular in the subsequent cultivation cycle.

After all this, it can be seen that the site-specifically recorded and mapped weights of the grains can be determined on the basis of the signals of the spectrometer 80a, 80b, and, with the addition of the yield values, further agronomic variables can be determined (number of grains per unit area and mass density, which, however, can also be measured on the basis of the spectra). These agronomic variables form a meaningful basis for the planning of subsequent measures, in particular the planting rate to be implemented site-specifically and an adapted spring fertilization in order to sufficiently influence the number of grains per area and thousand kernel mass and to bring them to the yield target. As explained above, these variables can be determined from any selection of the following measured and mapped values: yield, grain dimensions (or mass), and number of grains per unit area.

Those skilled in the art will recognize that it is common within the art to implement apparatuses and/or devices and/or processes and/or systems in the fashion(s) set forth herein, and thereafter use engineering and/or business practices to integrate such implemented apparatuses and/or devices and/or processes and/or systems into more comprehensive apparatuses and/or devices and/or processes and/or systems. That is, at least a portion of the apparatuses and/or devices and/or processes and/or systems described herein can be integrated into comprehensive apparatuses and/or devices and/or processes and/or systems via a reasonable amount of experimentation.

Although the present disclosure has been described in terms of specific examples and applications, persons skilled in the art can, considering this teaching, generate additional examples without exceeding the scope or departing from the spirit of the present disclosure described herein. Accordingly, it is to be understood that the drawings and description in this disclosure are proffered to facilitate comprehension of the present disclosure and should not be construed to limit the scope thereof.

As used herein, unless otherwise limited or modified, lists with elements that are separated by conjunctive terms (e.g., "and") and that are also preceded by the phrase "one or more of" or "at least one of" indicate configurations or arrangements that potentially include individual elements of the list, or any combination thereof. For example, "at least one of A, B, and C" or "one or more of A, B, and C" indicates the possibilities of only A, only B, only C, or any combination of two or more of A, B, and C (e.g., A and B; B and C; A and C; or A, B, and C).

It should also be noted that the different examples described herein can be combined in different ways. That is, parts of one or more examples can be combined with parts of one or more other examples. All of this is contemplated herein.

The invention claimed is:

1. A method for measuring at least one of a mass-specific variable or a size-specific variable of a grain crop in a first area and a second area of an agricultural field, comprising:
recording, based on information provided by a first sensor, a first mass flow rate of the grain crop in the first area and a second mass flow rate of the grain crop in the second area, wherein the first sensor is located at a first location on a housing of an agricultural vehicle, wherein a grain elevator of the agricultural vehicle releases the grain crop from the grain elevator to the first location to be measured by the first sensor, and wherein the grain elevator and the first location are on opposite sides of the housing;
recording, based on information provided by a second sensor, a first spectrum of the grain crop in the first area and a second spectrum of the grain crop in the second area, wherein the second sensor is operating in a near-infrared range, and wherein the second sensor is located at a second location different from the first location;
deriving a first mass-specific variable or a first size-specific variable from the first spectrum and a second mass-specific variable or a second size-specific variable from the second spectrum;
determining a first number of grains in the first area and a second number of grains in the second area based on the first and second mass flow rates and the first and second mass-specific variables or size-specific variables, wherein the first number of grains in the first area is greater than the second number of grains in the second area; and
determining an agricultural operation to be performed in the first area in a subsequent cultivation cycle, the agricultural operation determined based on a quotient between the first mass-specific variable or the first size-specific variable and the first number of grains, wherein the agricultural operation is performed in the first area at a decreased rate than in the second area based on the quotient.

2. The method of claim 1, wherein the second sensor is a spectrometer for sensing the first and second spectrums, and wherein deriving the first mass-specific variable or the first size-specific variable from the first spectrum and the second mass-specific variable or the second size-specific variable from the second spectrum further includes:
determining, with a controller, an ingredient of the grain crop in the first area using the first spectrum and the second area using the second spectrum; and
determining, with the controller, the first and second mass-specific variables or size-specific variables using the ingredient of the grain crop.

3. The method of claim 2, wherein the ingredient includes at least one of water, protein, starch, or a correlation thereof of the grain crop and the ingredient as an amount or content.

4. The method of claim 1, wherein the first and second mass-specific variables or size-specific variables relate to at least one of a thousand kernel weight or a mass density.

5. The method of claim 1, wherein the first and second mass-specific variables or size-specific variables relate to at least one of a hectoliter weight or dimensions of the grain crop.

6. The method of claim 4, wherein the agricultural vehicle is a harvester, and wherein the method further includes:
determining continuously the first and second mass-specific variables or size-specific variables during harvesting of the grain crop with the harvester; and
recording the first and second mass-specific variables or the size-specific variables georeferenced in a map corresponding to the first area and the second area.

7. The method of claim 6, further including determining continuously, during harvesting of the grain crop with the harvester, a third mass-specific variable or size-specific variable for a different crop from the grain crop being harvested.

8. The method of claim 6, further including:
measuring at least one additional ingredient of the grain crop; and
georeferencing in the map the at least one additional ingredient with the first and second mass-specific variables or the size-specific variables.

9. The method of claim 6, further including:
measuring a yield for at least a portion of a harvested field; and
storing the yield georeferenced in the map together with at least one of the first and second mass-specific variables or size-specific variables.

10. The method of claim 1, wherein the agricultural vehicle is a harvester, and wherein the first and second mass-specific variables or size-specific variables of the grain crop is determined while the agricultural field is being harvested with the harvester.

11. The method of claim 1, wherein the agricultural vehicle is a harvester, and wherein the first and second mass-specific variables or size-specific variables of the grain crop is determined after the agricultural field has been harvested with the harvester.

12. The method of claim 1, wherein the second location is on the housing of the agricultural vehicle, and the second location is at a different location on the housing than the first location.

13. An apparatus for measuring at least one of a mass-specific variable or a size-specific variable of a grain crop in a first area and a second area of an agricultural field, comprising:

a first sensor configured to measure a first mass flow rate of the grain crop in the first area and a second mass flow rate of the grain crop in the second area, wherein the first sensor is located at a first location on a housing of an agricultural vehicle, wherein a grain elevator of the agricultural vehicle releases the grain crop from the grain elevator to the first location to be measured by the first sensor, and wherein the grain elevator and the first location are on opposite sides of the housing;

a second sensor operating in a near-infrared range configured to measure a first spectrum of the grain crop in the first area and a second spectrum of the grain crop in the second area, wherein the second sensor is located at a second location different from the first location; and an evaluation device configured to:

derive a first mass-specific variable or a first size-specific variable from the first spectrum and a second mass-specific variable or a second size-specific variable from the second spectrum;

determine a first number of grains in the first area and a second number of grains in the second area based on the first and second mass flow rates and the first and second mass-specific variables or size-specific variables, wherein the first number of grains in the first area is greater than the second number of grains in the second area; and determine an agricultural operation to be performed in the first area in a subsequent cultivation cycle, the agricultural operation determined based on a quotient between the first mass-specific variable or the first size-specific variable and the first number of grains, wherein the agricultural operation is performed in the first area at a decreased rate than in the second area based on the quotient.

14. The apparatus of claim 13, wherein the second sensor is a spectrometer for sensing the first and second spectrums, and wherein, to derive the first mass-specific variable or the first size-specific variable from the first spectrum and the second mass-specific variable or the second size-specific variable from the second spectrum, the evaluation device is further configured to:

determine an ingredient of the grain crop in the first area using the first spectrum and the second area using the second spectrum; and determine the first and second mass-specific variables or size-specific variables using the ingredient of the grain crop.

15. The apparatus of claim 14, wherein the ingredient includes at least one of water, protein, starch, or a correlation thereof of the grain crop and the ingredient is an amount or content.

16. The apparatus of claim 13, wherein the agricultural vehicle is a harvester, and wherein the evaluation device is further configured to:

determine continuously during harvesting the first and second mass-specific variables or size-specific variables of the grain crop with the harvester in the agricultural field; and record the first and second mass-specific variables or the size-specific variables georeferenced in a map corresponding to the first area and the second area.

17. The apparatus of claim 16, wherein the evaluation device is further configured to determine continuously, during harvesting of the grain crop in the agricultural field with the harvester, a third mass-specific variable or size-specific variable for a different crop from the grain crop being harvested.

18. The apparatus of claim 17, wherein the evaluation device is configured to:

measure at least one ingredient of the different crop; and store the at least one ingredient georeferenced in the map with the third mass-specific variable or size-specific variable.

19. The apparatus of claim 18, wherein the evaluation device is configured to:

measure a yield for at least a portion of a harvested field; and store the yield georeferenced in the map together with at least one of the first, second, or third mass-specific variables or size-specific variables.

20. The apparatus of claim 13, wherein the second location is on the housing of the agricultural vehicle, and the second location is at a different location on the housing than the first location.

* * * * *